United States Patent [19]

Collins et al.

[11] Patent Number: 4,693,891

[45] Date of Patent: Sep. 15, 1987

[54] **VACCINE FOR *PSEUDOMONAS AERUGINOSA***

[75] Inventors: Michael S. Collins, Richmond; Grace C. Tsay, Walnut Creek; Richard L. Seng, San Francisco, all of Calif.

[73] Assignee: Miles Laboratories, Inc., Elkhart, Ind.

[21] Appl. No.: 773,915

[22] Filed: Sep. 9, 1985

[51] Int. Cl.$^4$ .............................................. A61K 39/02
[52] U.S. Cl. ........................................ 424/92; 424/88; 424/85; 424/87; 530/395; 530/402
[58] Field of Search ...................... 424/88, 92, 85, 87; 435/848, 852, 873, 875, 880, 859; 530/395, 402

[56] References Cited

U.S. PATENT DOCUMENTS

| | | | |
|---|---|---|---|
| 4,356,170 | 10/1982 | Jennings et al. | 424/85 |
| 4,372,883 | 2/1983 | Matuhashi et al. | 530/387 |
| 4,474,756 | 10/1984 | Mitsuhashi et al. | 424/88 |
| 4,578,458 | 3/1986 | Pier | 424/88 |
| 4,587,121 | 5/1986 | Collins et al. | 424/85 |

OTHER PUBLICATIONS

Seid et al., Preparation and Characterization . . . Conjugates" *JBC*, 1981, pp. 7305-7310.
Abst. (Biosis) Verloes et al., Successful Immuno Therapy . . . Chemotherapy" *Br J. Cancer* 43(2), 1981, pp. 201-209.

*Primary Examiner*—Morton Foelak
*Assistant Examiner*—Garnette D. Draper
*Attorney, Agent, or Firm*—Pamela A. Simonton

[57] ABSTRACT

There is disclosed an immunizing composition comprising a non-toxic polysaccharide isolated from gram-negative bacteria, especially from *Pseudomonas aeruginosa*, covalently coupled to a non-toxic protein from the gram-positive bacterium *Micrococcus luteus* by means of a 4-12 carbon moiety. To prepare the above immunizing agent, the lipid A portion of lipopolysaccharide from a gram-negative bacterium is separated to give a non-toxic polysaccharide. Reactive aldehyde groups are generated on the non-toxic polysaccharide by selective oxidation. The non-toxic polysaccharide is then covalently coupled to a non-toxic protein isolated from said gram-positive bacterium, *Micrococcus luteus*, by means of a polyfunctional compound having 4-12 carbon atoms and having at least two functional groups which are reactive to the aldehyde groups on the non-toxic polysaccharide and to the carboxylic groups on the non-toxic protein.

17 Claims, No Drawings

VACCINE FOR *PSEUDOMONAS AERUGINOSA*

BACKGROUND OF THE INVENTION

1. Field of the Invention: This invention relates to and has among its objects an immunizing composition, or vaccine, effective against gram-negative bacterial, especially *Pseudomonas aeruginosa*, infections and a method for producing said composition. Further objects of the invention will be evident from the following description wherein parts and percentages are by weight unless otherwise specified.

2. Description of the Prior Art: Gram-negative bacteria have two cell envelope membranes separated by a single thin layer of peptidoglycan. The inner or cytoplasmic membrane contains all known active transport systems and many of the cell envelop enzymes. The outer membrane is distinguished by a unique component lipopolysaccharide (lipid A plus polysaccharide) and a unique set of proteins. The O antigen-specific polysaccharide endows the particular bacterium with its main serological specificity. There is also a core polysaccharide, common to gram-negative bacteria, which is linked to a lipid component (lipid A). These complexes of lipid A, polysaccharide, and protein are antigenic and also exert toxic reactions in humans, thus being considered as endotoxins.

Vaccines containing lipopolysaccharides (LPS) from gramnegative bacteria have been used for immunization of humans against infection. The vaccines may comprise killed cells, cell lysate, or purified LPS; however, many are toxic.

Although infection with *Pseudomonas aeruginosa* (*P. aeruginosa*) is not common among the general population, *P. aeruginosa* infection is encountered very frequently in certain susceptible groups of patients. Burn victims and immunosuppressed cancer patients have been identified as having an unusually high risk of acquiring severe, and sometimes fatal, *P. aeruginosa* infection. *P. aeruginosa* infections are usually acquired during a hospital stay, not at home.

Antibiotics have been used to treat patients with *P. aeruginosa* infections. However, antibiotic treatment is very expensive, effectiveness is often uncertain, and organisms continue to develop resistance to antibiotics.

Vaccines have been prepared for a number of pathogenic bacteria, including *P. aeruginosa*. For example, U.S. Pat. No. 4,157,389 discloses a three component mixed vaccine against infections caused by *P. aeruginosa* which comprises as the antigens an infection-protective common antigen, Original Endotoxin Protein obtained from *P. aeruginosa*, an elastase toxoid obtained from *P. aeruginosa* and a protease toxoid obtained from *P. aeruginosa*.

Toxoids derived from protease and elastase of *P. aeruginosa* which are effective to prevent infections caused by *P. aeruginosa* are described in U.S. Pat. No. 4,160,023.

U.S. Pat. No. 3,987,164 discloses vaccine preparations comprising the cell wall protein component of *P. aeruginosa* as an active ingredient in a prophylactic pharmaceutical preparation.

Mink infection caused by *P. aeruginosa* can be prevented according to U.S. Pat. No. 4,096,245 by administering to mink a prophylactic preparation in the form of vaccine whose effective component mainly consists of protein and a small amount of lipid and sugar derived from *P. aeruginosa*.

Original endotoxin protein derived from *P. aeruginosa* is disclosed in U.S. Pat. No. 4,079,126. In the patented method of preparation the original endotoxin protein is processed with either proteolytic enzyme or reductant or further processed with proteolytic enzyme after it has been treated with reductant.

A bacterial endotoxin LPS of reduced toxicity covalently coupled to a protein antigen is described in U.S. Pat. No. 4,185,090. The coupling was effected by reaction with haloacylhalide. LPS acylated with an anhydride of a dibasic acid is detoxified; in combination with endotoxin polysaccharide covalently coupled to protein antigen it developed synergistic immunogenic effects.

In U.S. Pat. No. 4,285,936 a method is taught for isolating a non-toxic, high molecular weight polysaccharide antigen from the crude slime of a *P. aeruginosa* culture, and a method for inducing immunity in a host to said live organisms is described. Initially, bacterial cells are separated from the slime, which is dissolved in a phosphate buffer solution. After removal of dissolved contaminating nucleic acids, a lipid A portion of the contaminating LPS constituent is removed and precipitated by acetic acid hydrolysis. The remaining lipids are extracted with chloroform. Nearly all of the residual nucleic acids are then removed by digestion with nucleases, and the remaining protein extracted with phenol. The aqueous and phenol layers are separated, and the aqueous layer applied to a gel filter to isolate the polysaccharide antigen by column chromatography. The polysaccharide antigen was non-toxic and highly effective in inducing an immune response to the organism in a host.

SUMMARY OF THE INVENTION

We have discovered an immunizing composition comprising a non-toxic protein isolated from the gram-positive bacterium, *Micrococcus luteus*, which is covalently coupled by means of a polyfunctional compound having 4–12 carbon atoms to a non-toxic polysaccharide isolated from the group of gram-negative bacteria consisting of *Pseudomonas aeruginosa*, *Escherichia coli*, *Proteus sp*, *Serratia sp*, and *Klebsiellia sp* and the like, especially *Pseudomonas aeruginosa*. The novel immunizing agent of our invention is prepared by a method wherein the lipid A portion of a lipopolysaccharide derived from, for example, *Pseudomonas aeruginosa* is first separated to give a non-toxic polysaccharide free of lipid-A. The non-toxic polysaccharide is then selectively oxidized to produce aldehyde groups thereon. The selectively oxidized non-toxic polysaccharide is covalently coupled through the aldehyde groups to a non-toxic protein derived from said gram-positive bacterium, *Micrococcus luteus*, by means of a polyfunctional compound having 4–12 carbon atoms and containing at least two functional groups, one of which is reactive to the aldehyde groups on the non-toxic polysaccharide and the other of which is reactive to the carboxylic acid groups on the non-toxic protein. The compositions of the invention are useful as vaccines for parenteral administration for preventing bacterial infections and for administration to donors to raise the levels of antibody to a gram-negative bacterium of said donors. Blood collected from such donors may be pooled and fractionated to yield an immune serum globulin having a very high titer of said antibody. The high titer immune serum globulin may be administered to patients suffering from a particular gram-negative bacterial infection.

It is a particular advantage of the compositions of the invention that they exhibit a high degree of immunogenicity free of toxicity or endotoxic activity. Indeed, the immunogenicity of the immunizing agents is nearly equivalent to that of native lipopolysaccharide. By the phrase free of toxicity or endotoxin activity is meant the composition causes no weight loss or failure to gain weight in mice and has less than 1/1000th the activity of lipopolysaccharide in the Limulus amebocyte lysate assay.

It is important to note that the non-toxic polysaccharide is not immunogenic. Furthermore, mixtures of the non-toxic polysaccharide and the non-toxic Micrococcus protein are also inactive in stimulating antibody to the polysaccharide.

Lipopolysaccharides from gram-negative bacteria, for example, *Pseudomonas aeruginosa* are potent immunogens but highly toxic. Efforts to reduce toxicity of LPS have included chemical treatment such as alkaline or acid hydrolysis, to obtain lipid A-free polysaccharide which are not immunogenic. It is known that the immunogenicity of these lipid A-free polysaccharide antigens can be restored by covalently linking them to a protein carrier such as bovine serum albumin, rabbit globulin, tetanus toxoid and detoxified protein derived from a gram-negative bacterium. However, use of a protein carrier, such as bovine serum albumin, for preparing *Pseudomonas aeruginosa* polysaccharide conjugate vaccine is likely to cause serious immune reactions, such as autoimmune reactions, in humans due to bovine serum albumin sharing the same amino acid sequence with human serum albumin. Safety problems using detoxified protein derived from a gram-negative bacterium for preparing *Pseudomonas aeruginosa* polysaccharide conjugate vaccine have been observed and are believed to be due to trace amounts of toxic lipopolysaccharide contamination in these detoxified protein preparations. We have discovered that using non-toxic protein isolated from the lipopolysaccharide-free gram-positive bacterium, *Micrococcus luteus*, for preparing *Pseudomonas aeruginosa* polysaccharide conjugate vaccines provides vaccines which are free of lipopolysaccharide contamination and which are unlikely to cause autoimmune reactions in humans.

DESCRIPTION OF THE PREFERRED EMBODIMENTS

As mentioned above the immunizing composition of the invention comprises a non-toxic *Micrococcus luteus* protein covalently coupled by means of a 4-12 carbon compound to a non-toxic polysaccharide from gram negative bacteria, especially *Pseudomonas aeruginosa*. In the especially preferred embodiment of this invention, the non-toxic polysaccharide is isolated from *Pseudomonas aeruginosa* bacteria of at least one of Fisher immunotypes 1-7.

In the following description emphasis will be directed to an immunizing composition against *Pseudomonas aeruginosa*. This direction is by way of illustration only, not limitation. In its ambit the invention includes immunizing compositions against gram-negative bacteria such as *Escherichia coli*, Proteus sp, Serratia sp, Klebsiella sp et al.

In the first step in the preparation of the immunizing composition for *Pseudomonas aeruginosa* according to this invention, a non-toxic bacterial protein is extracted and purified from the gram-positive bacterium *Micrococcus luteus*. This may be accomplished by a variety of known chemical and physical methods. For example, one may use chemical methods such as guanadinium thiocyanate, zwitterionic detergent, lysozyme-ethylene diamene tetraacetic acid, sodium dodecyl sulfate, dimethyl formamide and the like. See, for example, Moldow et al, *J. Membrane Biol.*, 10 137–152 (1972), Hancock et al, *J. of Bacteriology*, 136, 381–390 (1978), Stinnett et al, ibid., 114, 399–407 (1973), and Robinson et al, *FEMS Microbiol. Lett.*, 5, 131–134 (1979). As examples of physical methods for extracting the protein from the protein-LPS complex, one may use such means as osmotic shock and sonication. Extraction of the protein may also be accomplished by a combination of the aforedescribed procedures. The extracted or isolated protein is sonicated and digested with ribonuclease. After ribonuclease digestion the protein mixture is applied to a Fractogel TSK HW-55 column (MCB Manufacturing Chemist, Inc.). The gel-excluded fraction (MW > 700,000) is discarded and the gel-included, or "retarded", fraction is eluted. The eluate containing the retarded fraction is treated with DEAE cellulose to remove ribonuclease and then subjected to diafiltration and ultrafiltration by PM-10 to remove low molecular species and concentrate the solution. The thus isolated non-toxic protein contains reactive carboxylic acid groups.

LPS may be isolated from *Pseudomonas aeruginosa* bacteria by known techniques such as (1) the phenol-water extraction method of Westphal et al, *Z. Naturforsch.*, 79, 148–155 (1952); (2) treatment with trichloroacetic acid reported by Staub, A. M. 1965. Bacterial lipido-proteino-polysaccharides ("O somatic antigens), In: Methods in Carbohydrate Chemistry, Vol. V, R. L. Wistler, J. N. Bemüller and M. L. Wolfrom, editors, Academic Press, New York, pp. 92–93; (3) treatment with aqueous butanol reported by Leive and Morrison, 1972, In: Methods in Enzymology, V. Ginsburg, editor, Vol. 28 (B), pp. 254–262; and the like. In the procedure of Westphal et al, LPS is isolated by extraction of *Pseudomonas aeruginosa* bacteria with a phenol-water mixture. The crude LPS is sonicated and digested with ribonuclease and deoxyribonuclease. After pronase digestion the LPS preparation may be subjected to diafiltration and ultrafiltration to remove low molecular species.

The so-isolated LPS is then treated to render it free of endotoxic activity using acid or alkali hydrolysis procedures.

The so-isolated LPS is next subjected to mild acid hydrolysis (Drewry et al, *Biochem. J.*, 149, 93–106, 1975) to remove the lipid A moiety, i.e., to prepare the non-toxic polysaccharide component free of lipid-A. For this purpose one may use acetic acid, hydrochloric acid and the like. Generally, the LPS is mixed with the acid in an aqueous medium in the proportion of about 1–5 parts of acid per part of LPS. For instance, the LPS may be mixed with a 0.5–3% aqueous solution of acid such that the concentration of LPS is about 1–10 mg per ml. The mixture is then heated at a temperature and for a time sufficient to remove the lipid A portion of the LPS, usually about 1–24 hours at 60°–100° C. The precipitate that forms comprises the lipid A portion of the LPS and is separated from the polysaccharide by conventional techniques such as centrifugation, decantation, filtration, and so forth to obtain the non-toxic polysaccharide. To assure removal of all lipid A, the supernatant containing the non-toxic polysaccharide is adjusted to about neutrality and extracted with a chlorohydrocarbon-alcohol mixture.

Non-toxic polysaccharides derived from *Pseudomonas aeruginosa* of Fisher Immunotypes 1, 2, 3, 4, 5 and 7 were prepared.

Non-toxic lipopolysaccharide derived from *Pseudomonas aeruginosa* of Fisher immunotype 6 was prepared by subjecting the so-isolated LPS to alkali hydrolysis by a modification of the procedure reported by M. Niwa et al, *J. Bacteriol.*, 97 (3), 1069–1077 (1969). Generally, according to this modified procedure, the LPS is mixed with an aqueous alkali solution, for example, a 0.1–1.0N aqueous sodium hydroxide solution, such that the concentration of LPS is about 1–10 mg per ml of mixture. The mixture is then heated at a temperature and for a time sufficient to remove the toxic ester-linked fatty acid portions of the LPS, such as about 30°–60° C. for 1–24 hours. Then, the non-toxic Fisher immunotype 6 lipopolysaccharide is adjusted to about neutral pH and further purified as described below. The above-described alkaline hydrolysis procedure is also suitable to prepare a non-toxic lipopolysaccharide derived from Fisher immunotype 4.

The aqueous layer containing the non-toxic polysaccharide free of lipid-A obtained by acid hydrolysis or non-toxic immunotype 6 lipopolysaccharide obtained by alkali hydrolysis as described above is concentrated and the non-toxic polysaccharide is purified by conventional techniques such as gel filtration, column chromatography and the like and then dried, e.g., by rotary evaporation or lyophilization.

Next, the non-toxic polysaccharide is selectively oxidized to generate aldehyde groups on the non-toxic polysaccharide. This may be accomplished by known procedures such as, for example, periodate oxidation as described by Sanderson et al, *Immunology*, 20, 1061–1065, (1971). Accordingly, the non-toxic polysaccharide is treated with a source of periodate ions, such as sodium periodate, potassium periodate, etc., in an amount and under conditions sufficient to selectively generate aldehyde groups on the non-toxic polysaccharide. Generally, an aqueous solution containing 1–20 mg/ml of non-toxic polysaccharide is mixed with 1–100 mM periodate at ambient temperature in the dark for 10–24 hours. The reaction is stopped by addition of ethylene glycol and the selectively oxidized non-toxic polysaccharide is purified by, for example, column chromatography or gel filtration and then treated to remove water by evaporation, lyophilization, or the like.

The selectively oxidized non-toxic polysaccharide is coupled to the non-toxic protein by means of a polyfunctional coupling compound having 4–12 carbon atoms and having functional groups reactive to the aldehyde groups of the non-toxic polysaccharide and to carboxylic acid groups of the non-toxic protein.

The polyfunctional coupling compound may be selected from compounds having at least two functional groups reactive with aldehyde and carboxylic acid groups such as, to name but a few, organic polyamines and especially diamines such as diaminobutane and 1,4-diaminobenzene, tolylene diisocyanate, and diisothiocyanate, dibasic carboxylic acids such as glutaric acid and suitable derivatives thereof, and a cyanogen halide such as cyanogen bromide. Preferably, the non-toxic protein is coupled with a 4–12 carbon compound containing at least two amino groups, i.e. an organic diamine. Excess coupling compound, such as a diamine, is generally employed. Thus, for example, about 3–20 parts of diamine may be mixed with one part of non-toxic protein in a buffered medium (pH 4.0–7.0) at a temperature of about 20°–40° C. for about 1–5 hours. Preferably, it is desirable to carry out the above coupling in the presence of an agent which will promote the coupling of the diamine by one of the two amino groups in the molecule to carboxylic acid groups on the non-toxic protein to obtain a derivatized non-toxic protein. The generally preferred coupling promoting agent is a carbodiimide such as that described by Cuatrecasas, *J. Biol. Chem.*, 245, 3059–3065 (1970). Usually, the carbodiimide is present in an amount of about 1–10 parts per part of diamine. After the above carbodiimide-promoted amide coupling reaction, the mixture is treated by conventional means such as dialysis or diafiltration to remove unreacted diamine compound and carbodiimide. Preferably, the reaction mixture above is dialyzed against a buffer system compatible with the reaction medium of the subsequent coupling of the derivatized non-toxic protein to the selectively oxidized non-toxic polysaccharide prepared as described above. Usually, the pH of the buffer system is about 7.0–9.0.

The selectively oxidized non-toxic polysaccharide is coupled via a Schiff's base reaction to the non-toxic Micrococcus protein derivatized with the above-described preferred 4–12 carbon diamine compound, which derivatized s non-toxic protein contains at least one amino group available for reaction with the aldehyde groups on the non-toxic polysaccharide. In the above coupling reaction of the derivatized non-toxic protein with the selectively oxidized non-toxic polysaccharide, it is desirable that the reaction be conducted in the presence of a reducing agent. For this purpose the preferred reducing agent is a cyanoborohydride such as that described by Borch et al, *J. Am. Chem. Soc.*, 93, 2897°–2904 (1971). In general, about 1–5 parts of dry selectively oxidized non-toxic polysaccharide and 2–20 parts of cyanoborohydride are mixed with 0.5–3 parts of derivatized non-toxic protein in a buffer system of pH about 7.0–9.0. The reaction mixture is then held at about 20°–50° C. for about 24–168 hours. The resulting product comprises the non-toxic Micrococcus protein covalently coupled to non-toxic, lipid A-free polysaccharide by means of a 4–12 carbon compound, the non-toxic protein being coupled to the 4–12 carbon compound by means of an amide linkage and the selectively oxidized non-toxic polysaccharide being coupled to the thus derivatized non-toxic protein at the 4–12 carbon compound portion by means of an amine linkage. This product may be purified by column chromatography, gel filtration, or the like.

The immunizing compositions of this invention are free of detectable endotoxic activity and toxicity but are highly immunogenic. In one aspect, a particular composition may be administered to a recipient such as a human or other animal in an amount effective to induce an immune response to one of the gram negative bacteria, for example, *Pseudomonas aeruginosa*. In another aspect, a particular composition may be administered to a recipient in an effective amount to prevent infections by one of the gram negative bacteria, for example, *Pseudomonas aeruginosa*. The amount effective to induce an immune response or to prevent infection may vary among recipients and also according to severity of the infection and may be administered in a single dose or in multiple doses. Generally, such effective amount is considered to be in the range of from about 0.001 mg to about 10 mg of immunizing composition, expressed as polysaccharide concentration, per 1 kg of recipient body weight per dose. The present compositions can be administered individually or in combination. Administration may be subcutaneous, intramuscular, or intracutaneous, with or without adjuvant.

Pharmaceutical preparations containing the immunizing compositions can be manufactured in the usual method for preparing vaccines for humans and other animals. For example, the immunizing composition may be dissolved in a suitable pharmaceutically-acceptable carrier, with or without pharmaceutically-acceptable adjuvant. As the carrier one may use distilled water, physiological saline and phosphate-buffered aqueous sodium chloride solution. Illustrative of adjuvants are aluminum hydroxide, aluminum phosphate, calcium phosphate, alum and Freund's incomplete adjuvant. The amount of adjuvant may be appropriately selected from the range of amounts being necessary and sufficient for increasing the immunoactivity.

An immunizing dose of the present material in mice is 5 μg low molecular weight ($5 \times 10^3 - 4 \times 10^4$) polysaccharide conjugated to 14−52 μg of Micrococcus protein.

An immunizing composition may also be used to produce anti-serum against the gram-negative bacterium to which it is directed. Antibody can be purified from the anti-serum. The anti-serum or antibody can be used to prevent infections caused by the particular gram-negative bacterium.

Furthermore, the blood or plasma collected from donors vaccinated with the present immunizing composition can be fractionated according to known techniques to yield a hyperimmune serum globulin having a high titer of antibody to a particular gram negative bacterium when compared to an immune serum globulin fractionated from blood or plasma obtained from donors to whom the composition of the invention was not administered. Such immune serum globulin may be administered to a patient intramuscularly or it may be treated by known procedures to render it intravenously injectable. For example, an immunizing composition derived from *Pseudomonas aeruginosa* may be administered to donors from whom blood or plasma is collected and fractionated to give a hyperimmune gamma globulin. The so-obtained immune serum globulin or gamma globulin may be administered intramuscularly to prevent infection by *Pseudomonas aeruginosa*. Alternatively, the hyperimmune serum globulins may be rendered intravenously injectable by methods well known in the art. Such hyperimmune gamma globulins have a titer of antibody against *Pseudomonas aeruginosa* of about 1:8,000−≧1:64,000 as determined in the enzyme linked immunosorbent assay (ELISA). These hyperimmune serum globulins were heretofore unavailable. Thus, the invention also comprises pharmaceutical preparations containing an immune serum globulin with an ELISA titer of antibody to a gram-negative bacteria, for example, *Pseudomonas aeruginosa*, of about 1:8,000−≧1:64,000.

The term "pharmaceutical preparation" is intended in a broader sense herein to include preparations containing a composition in accordance with this invention used not only for therapeutic purposes, but also for reagent purposes as are known in the art or for tissue culture purposes. The pharmaceutical preparation intended for therapeutic use should contain a therapeutic amount of composition, i.e., that amount necessary for preventative or curative health measures. If the pharmaceutical preparation is to be employed as a reagent, then it should contain reagent amounts of composition. Similarly, when used in tissue culture or a tissue culture medium the composition should contain an amount of the present composition sufficient to obtain the desired growth.

EXAMPLES

The invention is demonstrated further by the following illustrative examples.

EXAMPLE 1

Isolation and Preparation of Non-toxic Protein from *Micrococcus Luteus*

*Micrococcus luteus*— American Type Culture Collection (ATCC) #1-4698 was grown in Todd Hewitt broth medium to late log phase. Cells were killed with 1.0% formalin (vol./vol.) after which they were washed 2 times with phosphate buffered saline (pH 7.4), washed 1 time with water for injection, washed 2 times with acetone at −25° C. to remove soluble lipid, and finally lyophilized to dryness. Killed cells (17 g) were suspended with stirring in 6M guanidinium thiocyanate (350 ml) at pH 7.0 and 37° C. for 18-24 hours. Cell debris was removed by centrifugation and guanidinium thiocyanate was removed by dialysis against 6M urea. Urea was removed by dialysis against phosphate buffered saline. The precipitated protein was removed by centrifugation, solubilized in saline solution and the saline soluble fraction which contained the protein was concentrated about 10-fold through an Amicon® PM-10 filter (Amicon, Lexington, Mass.) and treated with ribonuclease (4 mg) in phosphate buffered saline pH 7.0 at 37° C. for 18-24 hours to remove contaminants of RNA. Ribonuclease digested protein was further purified on a Fractogel TSK HW-55 (2.6 cm × 100 cm) column. The "retarded" fractions from the Fractogel TSK HW-55 column, which contain proteins having a MW of about 10,000–25,000, were eluted and the eluates were combined and treated with 2 g of (wet) DEAE-cellulose in suspension and the pH adjusted to 9.0 by adding NaOH to remove ribonuclease. The DEAE mixture solid phase was removed and the resulting supernatant fluid was sterile filtered through a 0.2μ (Nalgene) membrane. The filtrate containing the purified protein fractions was concentrated through an Amicon PM-10 filter. There was thus obtained about 0.5 g of *Micrococcus luteus* protein for further use.

The Micrococcus protein was characterized as follows:

1. Absence of toxicity in mice.
2. On a weight basis, less than 1/4000th the activity of native LPS in the Limulus amebocyte lysate assay. Reference: Watson, S.W., J. Levin, T. J. Novitsky (eds), 1982. Endotoxins and their detection with the Limulus amebocyte lysate test. Proceedings of an International Conference on Endotoxin standards and Limulus amebocyte lysate use with parenteral drugs. Alan R. Liss, Inc., New York.
3. Reactive with antisera to *Micrococcus* protein.
4. In 12% SDS polyacrylamide gel eletrophoresis the protein is in the $10 \times 10^3 - 25 \times 10^3$ MW range.

EXAMPLE 2

Coupling of Diaminobutane to Non-toxic Micrococcus Protein

Micrococcus protein (60 mg) from Example 1 was dissolved in 10.0 ml of 0.05M phosphate buffered saline pH 7.2 was coupled with 1,4-diaminobutane (530 mg) in the presence of 530 mg 1-ethyl-3-(3-dimethyl-amino propyl)-carbodiimide. After 2 hours of gentle stirring at 21° C., the reaction mixture was dialyzed 4 times against 4 liters of 0.05M carbonate buffer pH 8.3 at 4° C. to remove excess reagent. The aminobutyl derivatized Micrococcus protein was characterized by 12-14% SDS polyacrylamide gel electrophoresis as in the 10,000 to 25,000 MW range.

EXAMPLE 3

Preparation of Non-toxic Polysaccharide from *Pseudomonas aeruginosa* (Immunotype 1)

*Pseudomonas aeruginosa* (Fisher-Devlin-Gnabasik immunotype 1) was grown in glucose-glutamine-salts medium. Cells were killed with 0.5% formalin. The killed cells were collected as a paste (a pellet) by centrifugation.

LPS was isolated from the thus prepared *Pseudomonas aeruginosa* cells by a modification of the phenol-water extraction procedure of Westphal et al, supra. About 180 g of cell paste of killed cells was suspended in about 1 L of watter for injection (WFI) and the resulting suspension was heated to about 65° C. Then, about 1 L of phenol, liquified at 65° C., was added to the heated cell paste-water(WFI) suspension. The cell paste-water-phenol suspension was heated at about 65° C. for about 15 minutes and was then cooled in an ice-water bath to a temperature of about 10°-12° C. The cooled cell paste-water-phenol suspension was centrifuged at 8000 ×g for about 60 minutes to obtain a top water layer, a middle layer containing solid cell debris, and a lower phenol layer. The water layer was removed and subjected for 3 days to dialysis against distilled water to remove residual phenol and low molecular weight bacterial substances.

The middle cell layer and lower phenol layer remaining after water removal above were re-suspended in about 1 L of water and the resulting second cell paste-water-phenol suspension was treated in a manner identical to that described above for the first such suspension.

Following dialysis, the LPS-containing water dialysates were combined and lyophilized, typically over a period of about 3 days, to obtain a crude LPS in a typical yield in repeated preparations in the range of about 1-2% based on starting amount of cell paste.

The so-isolated lyophilized crude LPS was suspended in water (WFI) and the suspension was sonicated for about 15 minutes to solubilize LPS micells. Then, the sonicated suspension was subjected t digestion by adding ribonuclease and deoxy ribonuclease in 0.1M acetate buffer at pH 5.0 and 35° C. for about 18-24 hours to destroy residual impurities of RNA and DNA. The resulting mixture was subjected to pronase (protease) digestion at pH 7.0 for about 24 hours. The LPS was purified from the mixture resulting from pronase digestion by diafiltration and ultrafiltration through an Amicon ® hollow fiber cartridge (e.g. Amicon HIX 50 or equivalent hollow fiber cartridge) to remove low molecular weight nucleic acids, peptides, and amino acids. Typically, the yield of purified LPS obtained as described above was about 80%, based on amount of crude LPS, in repeated preparations.

The purified LPS was treated in 1% acetic acid at a concentration of 2.5 mg/ml and then heated at 87° C. for 18 hours. The lipid A precipitate was removed by centrifugation. The acetic acid supernatant was adjusted to pH 7.0 with NaOH and extracted 3-5 times with two volumes of $CHCl_3$:methanol (2:1 vol./vol.) mixture to remove residual lipid A. The aqueous layer containing polysaccharide was concentrated by rotary evaporation under vacuum. The resulting non-toxic polysaccharide was further fractionated by BioGel-A5m (2.6 cm×100 cm) column chromatography. The retarded fraction from the BioGel-A5m chromatography was further purified on a Sephadex ® G-25 (2.6×100 cm) column. The major void volume fractions from the Sephadex ® G-25 column were combined and concentrated by rotary evaporation or lyophilization. Typically, the yield of non-toxic polysaccharide thus obtained was about 10%, based on amount of purified LPS, in repeated preparations.

The non-toxic polysaccharide was characterized as follows:

1. Free of endotoxin (LPS) activity.
2. Absence of toxicity in mice.
3. Less than 1/1000th the activity of LPS in the Limulus amebocyte lysate assay.
4. Reactive with antiserum to LPS in agar gel.
5. Unable to induce antibody or resistance to infection in mice.
6. MW of $5 \times 10^3 - 4 \times 10^4$.

By following substantially the procedure above except for starting with cell paste derived from *Pseudomonas aeruginosa* of Immunotypes 2, 5 and 7 there was produced non-toxic polysaccharide of *Pseudomonas aeruginosa* of immunotypes 2, 5 and 7 for producing an immunizing composition to these immunotypes.

EXAMPLE 4

Large Scale Preparation of Purified Lipopolysaccharide from *Pseudomonas aeruginosa* (Immunotypes 1-7)

This Example illustrates a procedure for producing purified *Pseudomonas aeruginosa* lipopolysaccharide, which is suitable for use in producing non-toxic polysaccharide as in Example 3 above, in relatively large quantities in but a fraction of the time required to produce the same quantities portion-wise.

According to this procedure, on day 1 about 180 g of cell paste or killed *Pseudomonas aeruginosa* cells, obtained as described in Example 3, was suspended in about 1 L of water for injection (WFI) and the suspension heated to about 65° C. Then, about 1 L of phenol, liquified at about 65° C, was added to the heated cell paste-water (WFI) suspension. The cell paste-water (WFI)-phenol suspension was heated at about 65° C. for about 15 minutes and then cooled in an icewater bath to about 10°-12° C. The cooled cell paste-water-phenol suspension was centrifuged at 7000 ×g for about 60 minutes to obtain a 3-layered (water-cell debrisphenol) centrifugate. The aqueous layer was removed and dialyzed against 50 L of water (WFI). The dialysis bag was then stored in a cold room at a temperature of about 10° C. for a period of 7 days including day 1.

On each of days 2-5, respectively, a fresh 180 g portion of cell paste of killed *Pseudomonas aeruginosa* cells was treated as described above. Typically, day 5 is a Friday and days 6 and 7 are Saturday and Sunday which, ordinarily, are non-working days.

Then, the dialysates from days 1–5 were pooled and concentrated, typically about 3-fold, by passing the dialysate pool through an Amicon ® hollow fiber cartridge (e.g., an Amicaon H5P30-43 cartridge).

To the thus-produced concentrate was added about 0.1 mg/ml of ribonuclease, about 0.1 mg/ml of deoxyribonuclease, and $MgCl_2$ to a concentration of about 0.01M and the pH was adjusted to about 7.0. To the resulting lmixture was added about 1 ml of toluene to prevent bacterial contamination and this mixture was held at about 37° C. for about 18 hours to complete day 8 treatment.

On day 9, protease was added to the so-prepared mixture from day 8 in an amount of about 0.1 mg/ml and the pH was adjusted to about 7.0 by adding 1N NaOH. The resulting mixture was held at about 37° C. for about 18 hours.

On days 10 and 11, the so-digested LPS concentrated having been protease treated was sterile filtered and the filtrate passed through an Amicon H5P30-43 hollow fiber cartridge. The permeate was washed with water until it had an $A_{280}$ of less than 0.15, then with 1.5M NaCl until the $A_{280}$ was less than 0.10 and then again with water until the $A_{280}$ was less than 0.10, and then it was frozen.

The frozen retenate was then lyophilized over a 3 day period to provide a resulting 5-fold yield compared with the yield from a single portion of starting cell paste which was obtained in about 40% of the time required to produce the same yield in 5 successive single portion preparations.

EXAMPLE 5

Selective Oxidation of Non-toxic Polysaccharide

Non-toxic polysaccharide (2.5 mg/ml) from Example 3 was oxidized with $NaIO_4$ (32 mM) at room temperature in the dark for 19 hours according to the procedure of Sanderson et al, *Immunology*, 20, 1061 (1971). At the end of reaction, ethylene glycol was added to expend the excess $NaIO_4$, and the solution was left at room temperature for an additional 3–4 hours. The selectively oxidized non-toxic polysaccharide was further purified by gel filtration (Sephadex ® G-25 column 1.0 cm × 100 cm). The major carbohydrate-content fractions were combined and lyophilized.

The selectively oxidized non-toxic polysaccharide was characterized as follows:
1. Increased number of aldehyde groups than native polysaccharide.
2. Reactive with antiserum to LPS.
3. No change in MW range.

EXAMPLE 6

Coupling of Selectively-oxidized Polysaccharide and Derivatized Non-toxic Micrococcus Protein Lyophilized selectively oxidized non-toxic polysaccharide (9.0 mg) from Example 4 and 50 mg of sodium cyanoborohydride were dissolved in 2.2 ml of 0.05M $NaHCO_3$, pH 8.3 containing 5.0 mg of derivatized non-toxic Micrococcus protein, and the resulting mixture was incubated at 37° C. for 74 hours. The reaction mixture was further purified by gel filtration on Sephadex ® G-100 column (100 cm × 1.0 cm).

The so obtained product was characterized as follows:

1. Purified non-toxic polysaccharide linked covalently to non-toxic Micrococcus protein.
2. Absence of toxicity in mice.
3. On a weight basis, less than 1/1000th the activity of LPS in the Limulus amebocyte lysate assay.
4. Reactive with antiserum to LPS and non-toxic Micrococcus protein.
5. Induces serum antibody and resistance to infection in mice.
6. In 14% SDS polyacrylamide gel electrophoresis the product was ≧200,000 MW range.

The biological activity of the above representative vaccines according to this invention was characterized as summarized in the following tables:

TABLE 1

Activity of *Pseudomonas aeruginosa* Fisher Immunotype (IT) 1 PS - Micrococcus Protein (MP) Conjugate Vaccines in the Limulus amebocyte lysate (LAL) Assay

| Substance Tested | Conc. In First Test Tube (μg/ml) | Highest Dilution Giving Gelation[a] |
|---|---|---|
| LPS[b] | 10 | 1:524,288 |
| Low Molecular Weight PS[c] | 10 | 1:8 |
| Aminobutyl - Micrococcus Protein (NMP)[d] | 100 | 1:8 |
| Aminobutyl - NMP:PS[e] Conjugate | 50–100[f] | 1:128 |

[a] = LAL sensitivity 0.03 ng/ml
[b] = LPS means "lipopolysaccharide"
[c] = PS means "polysaccharide", i.e. the "non-toxic" polysaccharide produced according to Example 3.
[d] = NMP means "non-toxic Micrococcus protein"; the Aminobutyl-Micrococcus Protein is the derivatized Micrococcus protein produced according to Example 2.
[e] = Aminobutyl - NMP:PS means the composition produced according to Example 6.
[f] = 40–90 μg of protein:10 μg of PS/ml

TABLE 2

Immunogenicity of the Components of *Pseudomonas aeruginosa* Fisher Immunotype 1 Polysaccharide: Micrococcus Protein Covalently Bonded Conjugate Vaccine

| Immunizing Substance | Dose[a] μg/ mouse | ELISA[b] Titer IgG | Cumulative Mortality No. Dead/Total | |
|---|---|---|---|---|
| | | | Active Immunity[c] | Passive Immunity[d] |
| Fr. IIa Polysaccharide[e] | 5 | <1:50 | 10/10 | 7/10 |
| Fr. IIb Polysaccharide[e] | 5 | <1:50 | 9/10 | 5/8 |
| Fr. IIa Polysaccharide:Micrococcus Protein Conjugate[f] | 5.0:22.8 | 1:800 | 2/10 | 1/9 |
| Fr. IIb Polysaccharide:Micrococcus Protein Conjugate[f] | 4.0:27.8 | 1:400 | 2/10 | 0/9 |
| Saline | | | 8/10 | 5/8 |

[a] Mice were immunized by subcutaneous injection on days 1, 7, 14, 21 and 28.
[b] The dilution of serum giving an $A^*_{450\ nm}$ of 0.10. Serum obtained 5 days after the 5th immunization.
[c] Immunized burned mice 49 days after the 5th immunization were challenged with 2,450 CFU of *Pseudomonas aeruginosa* IT 1 and observed cumulative mortality for 15 days. The immunizing substance was dissolved in phosphate buffered saline for injection into the mice.
[d] Mice were passively immunized with 0.1 ml serum. Pentobarbital anathetized mice giving a 10% dorsal full thickness burn with a gas-flame then challenged with 1,400 cells in 0.5 ml saline by subcutaneous injection in the burn site.
[e] Fraction (Fr.) IIa polysaccharide (MW = 1.8–30 × $10^3$) and Fraction (Fr.) IIb polysaccharide (MW = 1.2–1.8 × $10^3$) were collected from the fractionations of *P. aeruginosa* immunotype 1 low molecular weight polysaccharides on Sephadex G-25 column as described in Example 3.
[f] Conjugate produced as described in Example 6.

natant containing the non-toxic polysaccharide is adjusted to about neutrality and extracted with a chlorohydrocarbon-alcohol mixture.

Non-toxic polysaccharides derived from *Pseudomonas aeruginosa* of Fisher Immunotypes 1, 2, 3, 4, 5 and 7 were prepared.

Non-toxic lipopolysaccharide derived from *Pseudomonas aeruginosa* of Fisher immunotype 6 was prepared by subjecting the so-isolated LPS to alkali hydrolysis by a modification of the procedure reported by M. Niwa et al, *J. Bacteriol.*, 97 (3), 1069–1077 (1969). Generally, according to this modified procedure, the LPS is mixed with an aqueous alkali solution, for example, a 0.1–1.0N aqueous sodium hydroxide solution, such that the concentration of LPS is about 1–10 mg per ml of mixture. The mixture is then heated at a temperature and for a time sufficient to remove the toxic ester-linked fatty acid portions of the LPS, such as about 30°–60° C. for 1–24 hours. Then, the non-toxic Fisher immunotype 6 lipopolysaccharide is adjusted to about neutral pH and further purified as described below. The above-described alkaline hydrolysis procedure is also suitable to prepare a non-toxic lipopolysaccharide derived from Fisher immunotype 4.

The aqueous layer containing the non-toxic polysaccharide free of lipid-A obtained by acid hydrolysis or non-toxic immunotype 6 lipopolysaccharide obtained by alkali hydrolysis as described above is concentrated and the non-toxic polysaccharide is purified by conventional techniques such as gel filtration, column chromatography and the like and then dried, e.g., by rotary evaporation or lyophilization.

Next, the non-toxic polysaccharide is selectively oxidized to generate aldehyde groups on the non-toxic polysaccharide. This may be accomplished by known procedures such as, for example, periodate oxidation as described by Sanderson et al, *Immunology*, 20, 1061–1065, (1971). Accordingly, the non-toxic polysaccharide is treated with a source of periodate ions, such as sodium periodate, potassium periodate, etc., in an amount and under conditions sufficient to selectively generate aldehyde groups on the non-toxic polysaccharide. Generally, an aqueous solution containing 1–20 mg/ml of non-toxic polysaccharide is mixed with 1–100 mM periodate at ambient temperature in the dark for 10–24 hours. The reaction is stopped by addition of ethylene glycol and the selectively oxidized non-toxic polysaccharide is purified by, for example, column chromatography or gel filtration and then treated to remove water by evaporation, lyophilization, or the like.

The selectively oxidized non-toxic polysaccharide is coupled to the non-toxic protein by means of a polyfunctional coupling compound having 4–12 carbon atoms and having functional groups reactive to the aldehyde groups of the non-toxic polysaccharide and to carboxylic acid groups of the non-toxic protein.

The polyfunctional coupling compound may be selected from compounds having at least two functional groups reactive with aldehyde and carboxylic acid groups such as, to name but a few, organic polyamines and especially diamines such as diaminobutane and 1,4-diaminobenzene, tolylene diisocyanate, and diisothiocyanate, dibasic carboxylic acids such as glutaric acid and suitable derivatives thereof, and a cyanogen halide such as cyanogen bromide. Preferably, the non-toxic protein is coupled with a 4–12 carbon compound containing at least two amino groups, i.e. an organic diamine. Excess coupling compound, such as a diamine, is generally employed. Thus, for example, about 3–20 parts of diamine may be mixed with one part of non-toxic protein in a buffered medium (pH 4.0–7.0) at a temperature of about 20°–40° C. for about 1–5 hours. Preferably, it is desirable to carry out the above coupling in the presence of an agent which will promote the coupling of the diamine by one of the two amino groups in the molecule to carboxylic acid groups on the non-toxic protein to obtain a derivatized non-toxic protein. The generally preferred coupling promoting agent is a carbodiimide such as that described by Cuatrecasas, *J. Biol. Chem.*, 245, 3059–3065 (1970). Usually, the carbodiimide is present in an amount of about 1–10 parts per part of diamine. After the above carbodiimide-promoted amide coupling reaction, the mixture is treated by conventional means such as dialysis or diafiltration to remove unreacted diamine compound and carbodiimide. Preferably, the reaction mixture above is dialyzed against a buffer system compatible with the reaction medium of the subsequent coupling of the derivatized non-toxic protein to the selectively oxidized non-toxic polysaccharide prepared as described above. Usually, the pH of the buffer system is about 7.0–9.0.

The selectively oxidized non-toxic polysaccharide is coupled via a Schiff's base reaction to the non-toxic Micrococcus protein derivatized with the above-described preferred 4–12 carbon diamine compound, which derivatized s non-toxic protein contains at least one amino group available for reaction with the aldehyde groups on the non-toxic polysaccharide. In the above coupling reaction of the derivatized non-toxic protein with the selectively oxidized non-toxic polysaccharide, it is desirable that the reaction be conducted in the presence of a reducing agent. For this purpose the preferred reducing agent is a cyanoborohydride such as that described by Borch et al, *J. Am. Chem. Soc.*, 93, 2897°–2904 (1971). In general, about 1–5 parts of dry selectively oxidized non-toxic polysaccharide and 2–20 parts of cyanoborohydride are mixed with 0.5–3 parts of derivatized non-toxic protein in a buffer system of pH about 7.0–9.0. The reaction mixture is then held at about 20°–50° C. for about 24–168 hours. The resulting product comprises the non-toxic Micrococcus protein covalently coupled to non-toxic, lipid A-free polysaccharide by means of a 4–12 carbon compound, the non-toxic protein being coupled to the 4–12 carbon compound by means of an amide linkage and the selectively oxidized non-toxic polysaccharide being coupled to the thus derivatized non-toxic protein at the 4–12 carbon compound portion by means of an amine linkage. This product may be purified by column chromatography, gel filtration, or the like.

The immunizing compositions of this invention are free of detectable endotoxic activity and toxicity but are highly immunogenic. In one aspect, a particular composition may be administered to a recipient such as a human or other animal in an amount effective to induce an immune response to one of the gram negative bacteria, for example, *Pseudomonas aeruginosa*. In another aspect, a particular composition may be administered to a recipient in an effective amount to prevent infections by one of the gram negative bacteria, for example, *Pseudomonas aeruginosa*. The amount effective to induce an immune response or to prevent infection may vary among recipients and also according to severity of the infection and may be administered in a single dose or in multiple doses. Generally, such effective amount is

TABLE 5-continued

Immunogenicity of the Components of *Pseudomonas aeruginosa* Fisher Immunotype 6 Non-toxic Lipopolysaccharide: Micrococcus Protein Covalently Bonded Conjugate Vaccine

| Immunizing Substance | Dose[a] μg/mouse | ELISA[b] Titer IgG | Cumulative Mortality No. Dead/Total | |
|---|---|---|---|---|
| | | | Active Immunity[c] | Passive Immunity[d] |
| Aminobutyl - NMP: N-LPS conjugate- | 10.4:75.3 | 1:800 | 1/13 | 8/10 |
| Saline | | <1:200 | 11/13 | 9/9 |

[a]Mice were immunized by subcutaeous injection on days 1, 7, 14, 21 and 28.
[b]The dilution of serum giving an A*$_{450\,nm}$ of 0.10. Serum obtained 5 days after the 5th immunization.
[c]Immunized burned mice 44 days after the 5th immunization were challenged with 185 CFU of *Pseudomonas aeruginosa* IT 6 and observed cumulative mortality for 15 days. The immunizing substance was dissolved in phosphate buffered saline for injection into the mice.
[d]Burned mice were passively immunized with 0.1 ml serum and challenged with 210 CFU of *Pseudomonas aeruginosa* immunotype 6.
[e]N-LPS means "non-toxic lipopolysaccharid", i.e. the non-toxic lipopolysaccharide produced acoording to Example 7.
[f]Aminobutyl - NMP:N-LPS means the composition produced according to Example 9.

TABLE 6

Induction of Passively Protective Antibody with *Pseudomonas aeruginosa* Immunotype 6 Non-toxic lipopolysaccharide (N-LPS) - Micrococcus Protein Conjugate Vaccine[a]: Effect of Booster Injection

| Days of Immunization (10.0 μg N-LPS/dose) | Bleeding Day after first Immunization | ELISA[b] Titer IgGl | Cumulative Mortality[c] No. Dead/Total Passive Immunity |
|---|---|---|---|
| preimmune | −2 | <1:200 | 7/8 |
| 1 | — | — | — |
| 7 | — | — | — |
| 14 | 19 | 1:800 | 5/10 |
| 21 | — | — | — |
| 28 | 33 | 1:400 | 8/10 |
| | 47 | 1:400 | 8/10 |

[a]This composition (conjugate vaccine) was produced according to Example 9.
[b]Titer determined by linear regression of absorbance (A*$_{450\,nm}$ = 0.10) of 2-fold dilution of sera.
[c]Burned mice were passively immunized with 0.1 ml serum and challenged with 210 CFU of *Pseudonas aeruginosa* immunotype 6.

What is claimed is:

1. An immunizing composition effective against gram negative bacteria selected from the group consisting of *Pseudomonas aeruginosa, Esherichia coli*, Proteus sp, Serratia sp, and Klebsiella sp, and free from toxicity and endotoxin activity comprising (a) a non-toxic protein having reactive carboxylic acid groups isolated from the gram-positive bacterium, *Micrococcus luteus;* and (b) a member selected from a non-toxic polysaccharide and a non-toxic lipopolysaccharide isolated from said gram negative bacteria, said non-toxic polysaccharide or non-toxic lipopolysaccharide having been selectively oxidized to provide reactive aldehyde groups thereon, wherein the non-toxic protein and the non-toxic polysaccharide or non-toxic lipopolysaccharide are covalently coupled by means of a polyfunctional compound having a 4–12 carbon atoms and containing at least two functional groups, one of which is reactive to the aldehyde groups on the selectively oxidized non-toxic polysaccharide or non-toxic lipopolysaccharide and the other of which is reactive to the carboxylic acid groups on the non-toxic protein.

2. An immunizing composition effective against *Pseudomonas aeruginosa* and free from toxicity and endotoxin activity comprising (a) a non-toxic protein having reactive carboxylic acid groups isolated from the gram-positive bacterium, *Micrococcus luteus;* and (b) a member selected from a non-toxic polysaccharide and a non-toxic lipopolysaccharide isolated from *Pseudomonas aeruginosa* bacteria of at least one of Fisher immunotypes 1–7, said non-toxic polysaccharide or non-toxic lipopolysaccharide having been selectively oxidized to provide reactive aldehyde groups thereon, wherein the non-toxic protein and the non-toxic polysaccharide or non-toxic lipopolysaccharide are covalently coupled by means of a polyfunctional compound having 4–12 carbon atoms and containing at least two functional groups, one of which is reactive to the aldehyde groups on the selectively oxidized non-toxic polysaccharide or non-toxic lipopolysaccharide and the other of which is reactive to the carboxylic acid groups on the non-toxic protein.

3. An immunizing composition according to claim 2 wherein the polyfunctional compound is selected from the group consisting of (a) an organic polyamine; (b) tolylene diisocyanate; (c) tolylene diisothiocyanate; (d) a dibasic carboxylic acid and suitable derivatives thereof; and (e) a cyanogen halide.

4. An immunizing composition according to claim 2 wherein the polyfunctional compound is an organic polyamine containing at least two amino groups.

5. An immunizing composition according to claim 4 wherein the polyfunctional compound is an organic diamine.

6. An immunizing composition according to claim 5 wherein the organic diamine is present in the relative proportions of about 3–20 parts of diamine per 1 part of non-toxic protein and the non-toxic polysaccharide or non-toxic lipopolysaccharide is present in the relative proportion of about 1–5 parts of dry non-toxic polysaccharide or non-toxic lipopolysaccharide per 0.5–3 parts of derivatized non-toxic protein resulting from the reaction of the diamine with the non-toxic protein.

7. A pharmaceutical preparation comprising the immunizing composition according to claim 2 and a pharmaceutically acceptable carrier.

8. A method for preparing hyperimmune serum globulin having a high titer of antibody to *Pseudomonas aeruginosa* which comprises
   (a) adminstering to a donor an amount of an immunizing compostion effective against *Pseudomonas aeruginosa* and free from toxicity and endotoxin activity comprising (a) a non-toxic protein having reactive carboxylic acid groups isolated from the gram-positive bacterium, *Micrococcus luteus;* and (b) a member selected from a non-toxic polysaccharide and a non-toxic lipopolysaccharide isolated from *Pseudomonas aeruginosa* bacteria of at least one of Fisher immunotypes 1–7, said non-toxic polysaccharide or non-toxic lipopolysaccharide having been selectively oxidized to provide reactive aldehyde groups thereon, wherein the non-toxic protein and the non-toxic polysaccharide or non-toxic lipopolysaccharide are convalently coupled by means of a polyfunctional compound having 4–12 carbon atoms and containing at least two functional groups, one of which is reactive to the aldehyde groups on the selectively oxidized non-toxic polysaccharide or non-toxic lipopolysaccharide and the other of which is reactive to the carboxylic acid groups on the non-toxic protein, in an amount sufficient to raise the antibody to *Pseudomonas aeruginosa* to a level higher than normally found in the blood of said donor, p1 (b) obtaining blood from said donor during a period in which the blood of said donor exhibits a higher than normal titer of antibody against *Pseudomonas aeruginosa,* and (c) fractionating said blood to give an immune serum globulin having a high titer of antibody to *Pseudomonas aeruginosa* when compared to an immune serum globulin fractionated from blood obtained from a donor to whom the composition according to claim 1 was not administered.

9. A hyperimmune serum globulin produced according to the method of claim 8 having a titer of antibody to *Pseudomonas aeruginosa* of about 1:8,000 to at least about 1:64,000.

10. A method for preparing the immunizing composition according to claim 2 which comprises
(a) treating a lipopolysaccharide derived from *Pseudomonas aeruginosa* to give at least one of a non-toxic polysaccharide and non-toxic lipopolysaccharide free of endotoxin activity,
(b) selectively oxidizing the non-toxic polysaccharide or non-toxic lipopolysaccharide from step (a) to produce reactive aldehyde groups thereon,
(c) extracting and purifying a non-toxic protein derived from the gram-positive bacterium *Micrococcus luteus,* said non-toxic protein containing reactive carboxylic acid groups, and
(d) covalently coupling said non-toxic protein to said selectively oxidized non-toxic polysaccharide or non-toxic lipopolysaccharide by means of a polyfunctional compound having 4–12 carbon atoms and containing at least two functional groups, one of which is reactive to the aldehyde groups on the non-toxic polysaccharide and the other of which is reactive to the carboxylic acid groups on the non-toxic protein.

11. The method according to claim 10 wherein the polyfunctional compound is a compound having 4–12 carbon atoms and containing at least two amino groups.

12. The method according to claim 10 wherein about 3–20 parts of an organic diamine as the polyfunctional compound is mixed, under conditions which effect chemical reaction between amino and carboxylic acid groups, with 1 part of non-toxic protein in a buffered medium at pH about 5.0–7.0 and at a temperature of about 20°–40° C. for about 1–5 hours in the presence of a catalytic amount of a coupling agent which will promote the reaction of one of the two amino groups in the diamine molecule with carboxylic acid groups to obtain a derivatized non-toxic protein and, following removal of unreacted diamine and coupling agent, further mixing said derivatized non-toxic protein with about 1–5 parts of at least one of dry selectively oxidized non-toxic polysaccharide and non-toxic lipopolysaccharide and about 2–20 parts of cyanoborohydride reducing agent are mixed under conditions which will effect chemical reaction between amino and aldehyde groups with about 0.5–3 parts of derivatized non-toxic protein so as to couple the derivatized non-toxic protein and the selectively oxidized non-toxic polysaccharide or non-toxic lipopolysaccharide.

13. The method according to claim 12 wherein the diamine is diaminobutane and the coupling agent is a carbodiimide.

14. A composition produced by the method according to claim 10.

15. A composition produced by the method according to claim 11.

16. A composition produced by the method according to claim 12.

17. A composition produced by the method according to claim 13.

* * * * *